United States Patent
Bihler et al.

(10) Patent No.: US 10,068,681 B2
(45) Date of Patent: Sep. 4, 2018

(54) METHOD FOR PRODUCING AN ELECTRODE LEAD OR A CATHETER, AND ASSOCIATED SEMIFINISHED PRODUCT

(71) Applicant: BIOTRONIK SE & Co. KG, Berlin (DE)

(72) Inventors: Eckardt Bihler, Winterthur (CH); Marc Hauer, Uster (CH); René Toelke, Zurich (CH)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 15/399,098

(22) Filed: Jan. 5, 2017

(65) Prior Publication Data
US 2017/0221602 A1  Aug. 3, 2017

(30) Foreign Application Priority Data
Jan. 29, 2016 (DE) .......................... 10 2016 101 619

(51) Int. Cl.
*H01B 7/02* (2006.01)
*H01R 43/20* (2006.01)
(Continued)

(52) U.S. Cl.
CPC ............. *H01B 7/02* (2013.01); *A61B 5/6852* (2013.01); *A61N 1/02* (2013.01); *H01R 43/005* (2013.01);
(Continued)

(58) Field of Classification Search
CPC ........ H01B 7/02; A61N 1/02; B29C 65/7814; B29C 66/10; H01R 43/005; H01R 43/20; H02G 1/14; H02G 15/02
(Continued)

(56) References Cited

U.S. PATENT DOCUMENTS

| | | | |
|---|---|---|---|
| 4,589,584 A | | 5/1986 | Christiansen et al. |
| 4,873,411 A | * | 10/1989 | Saen ...................... B23K 11/14 |
| | | | 219/91.21 |

(Continued)

FOREIGN PATENT DOCUMENTS

| | | |
|---|---|---|
| DE | 1 765 434 A | 7/1971 |
| DE | 17 65 434 A | 7/1971 |

(Continued)

OTHER PUBLICATIONS

Partial European Search Report and Annex to the European Search Report on European Patent Application No. EP 17 15 1704.8, dated Jul. 11, 2017 (14 pages).

(Continued)

*Primary Examiner* — Timothy Thompson
*Assistant Examiner* — Charles Pizzuto
(74) *Attorney, Agent, or Firm* — Buchanan Ingersoll & Rooney PC (57) ABSTRACT

A method for producing a medical electrode lead or a catheter, and also to an associated semifinished product. The semifinished product for this purpose includes a cable having at least one electrical conductor, which is embedded in a sheath made of an electrically insulating, thermoplastic material. It is characterized in that the cable, at least at one cable end, forms a connection point, via which the conductor can be attached permanently and non-detachably to further components, wherein part of the surface of the conductor is exposed in the region of the connection point and forms a contact face, and the sheath has, in the region of the connection point, a recess that is continuous in the longitudinal direction of the cable.

15 Claims, 4 Drawing Sheets

(51) Int. Cl.
*H02G 1/14* (2006.01)
*H02G 15/02* (2006.01)
*A61N 1/02* (2006.01)
*H01R 43/00* (2006.01)
*H01R 43/24* (2006.01)
*A61B 5/00* (2006.01)
*A61N 1/05* (2006.01)
*A61M 25/00* (2006.01)

(52) U.S. Cl.
CPC ............ *H01R 43/20* (2013.01); *H01R 43/24* (2013.01); *H02G 1/14* (2013.01); *H02G 15/02* (2013.01); *A61B 2562/0209* (2013.01); *A61B 2562/12* (2013.01); *A61B 2562/125* (2013.01); *A61B 2562/222* (2013.01); *A61B 2562/225* (2013.01); *A61M 25/0009* (2013.01); *A61N 1/05* (2013.01); *H01R 2201/12* (2013.01)

(58) Field of Classification Search
USPC ....................................................... 174/74 R
See application file for complete search history.

(56) References Cited

U.S. PATENT DOCUMENTS

| | | | | |
|---|---|---|---|---|
| 5,097,100 | A * | 3/1992 | Jackson ................. | H01R 4/029 174/126.2 |
| 6,610,930 | B1 * | 8/2003 | Seuntjens ............. | B21C 37/042 174/94 R |
| 2005/0253249 | A1 * | 11/2005 | Chen ................. | G02F 1/136286 257/700 |
| 2009/0017197 | A1 * | 1/2009 | Zhang ................. | G01N 33/5438 427/126.5 |
| 2010/0037457 | A1 | 2/2010 | Weissenrieder et al. | |
| 2015/0206625 | A1 * | 7/2015 | Kumada ............ | H01B 11/1826 174/102 C |

FOREIGN PATENT DOCUMENTS

| | | |
|---|---|---|
| DE | 1 790 116 A | 1/1972 |
| DE | 17 90 116 A | 1/1972 |
| DE | 43 01 692 A1 | 7/1993 |
| DE | 602 14 789 T2 | 9/2007 |
| DE | 10 2016 101 619 A1 | 8/2017 |
| GB | 2 531 435 A | 4/2016 |
| GB | 2531435 A | 4/2016 |
| WO | WO 2015/093247 A1 * | 6/2015 ............ H01R 4/188 |
| WO | 2015172729 A1 | 11/2015 |

OTHER PUBLICATIONS

European Search Report and Annex to the European Search Report on European Patent Application No. EP 17 15 1704.8, dated Sep. 14, 2017 (13 pages).

German Search Report for German Case No. DE 10 2016 101 619.5, dated Nov. 4, 2016 (7 pages).

German Search Report for German Case No. DE 10 2017 117 674.8, dated Aug. 29, 2017 (9 pages).

* cited by examiner

METHOD FOR PRODUCING AN ELECTRODE LEAD OR A CATHETER, AND ASSOCIATED SEMIFINISHED PRODUCT

CROSS-REFERENCE TO RELATED APPLICATIONS

This patent application claims the benefit of and priority to co-pending German Patent Application No. DE 10 2016 101 619.5, filed on Jan. 29, 2016 in the German Patent Office, which is hereby incorporated by reference in its entirety.

TECHNICAL FIELD

The present invention relates to a method for producing a medical electrode lead or a catheter, and also to an associated semifinished product.

BACKGROUND

In the field of electrical engineering, a large number of techniques have been developed with which electrical contact can be produced in a permanent manner. The term "contacting" is understood here to mean a secure electrical connection between two conductors. The purpose of an electrical connection is thus to conduct an electrical current via this contact point. Here, there is of course a contact resistance, which normally should be as low as possible.

The electrical connection technique is a key factor in the production of electrical modules and ultimately electrical apparatuses and ensures the connection of the components to one another and also the connection to the outside world. A large number of electrical contact points are also sometimes found inside components.

Non-detachable electrical connections or connection techniques include, for example:
  welded connections (welding),
  bonded connections, bonding,
  adhesive connections, adhesion (with conductive adhesive),
  press-fit connection, crimp connectors, butt connectors (for example, by means of cable shoes or press-fit sleeves), and
  riveted connections.

A further subdivision can be made into soldered connections and solder-free connections. For medical products intended for intracorporeal use, solder-free connections should preferably be created.

Depending on the configuration in the design phase, detachability or conditional detachability is provided in the case of larger and more costly apparatuses. In the case of products for one-time use, the selected connection method is focused rather on the economical production process for the manufacturer and hardly takes reparability into consideration at all. Catheters and electrodes for medical use belong to the more recent product range, in which flexible materials in particular are used. These products thus generally include cable-like parts, in which there are embedded one or more conductors in a flexible insulator. The production of such flexible conductor portions for catheters and electrodes is currently subject to a length restriction on account of the manufacturing process. Cable portion lengths from approximately 60 cm and more for this reason have to be created by combining a number of individual portions. The electrical connection of the individual portions must be permanent and reliable and should use only biocompatible materials. There is thus an ongoing need for an economical connection technique that is suitable for medical use.

The present invention is directed toward overcoming one or more of the above-mentioned problems.

SUMMARY

One or more disadvantages of the prior art are eliminated are at least mitigated with the aid of the method according to the present invention for producing an electrode lead or a catheter, and also the associated semifinished product. The semifinished product comprises a cable having at least one electrical conductor, which is embedded in a sheath made of an electrically insulating, thermoplastic material. It is characterized in that the cable, at least at one cable end, forms a connection point, via which the conductor can be attached permanently and non-detachably to further components, wherein:
  part of the surface of the conductor is exposed in the region of the connection point and forms a contact face, and
  the sheath has, in the region of the connection point, a recess that is continuous in the longitudinal direction of the cable.

The method according to the present invention for producing an electrode line or a catheter comprises the following steps accordingly:
  a) providing a first and second semifinished product, wherein each semifinished product comprises a cable having at least one electrical conductor, which is embedded in a sheath made of an electrically insulating, thermoplastic material, and characterized in that the cable, at least at one cable end, forms a connection point via which the conductor can be attached permanently and non-detachably to further components, wherein:
    part of the surface of the conductor is exposed in the region of the connection point and forms a contact face, and
    the sheath has, in the region of the connection point, a recess that is continuous in the longitudinal direction of the cable,
    and wherein a contour of the recesses of the connection point of the first semifinished product corresponds substantially to a contour of the sheath in the region of the connection point of the second semifinished product;
  b) positioning the two semifinished products in a tool in such a way that the connection points rest on one another in a matching manner, such that the contact faces of the two conductors contact one another and the contours of the connection points of the two semifinished products engage with one another; and
  c) thermally melting the thermoplastic material in the region of the connection points.

The present invention is based on the finding that a reliable electrical connection of the individual components of a flexible medical electrode or a flexible catheter can be produced with the aid of specifically formed connection points and without the addition of further materials in order to create the connection. Specifically, the semifinished products necessary for this purpose have a cable, inside which one or more electrical conductors for signal transfer or current conduction are disposed. At least at one end of the cable there is disposed the aforementioned connection point. The second cable end can also have a connection point, such that the semifinished product is a middle piece when manufacturing an electrode and a catheter from at least three individual parts. If this semifinished product is an end piece, the second cable end, for example, carries elements which serve to sense the later function of the electrode or catheter.

The connection point provided at the cable end of the semifinished product serves to create a permanent and non-detachable electrical connection between two semifinished products having complementary connection points. For this purpose, part of the surface of the conductor is freely accessible in the region of the connection point. The electrical contact to a second semifinished product having a complementary connection point will be created later via this freely accessible region. It should be noted that the electrical conductor is only partially exposed over the entire length of the connection point, i.e., at least an underside of the three-dimensional conductor structure is always covered by part of this sheath made of the electrically insulating thermoplastic material. In other words, the parts of the sheath still present in the region of the connection point serve as carrier for the electrical conductor. A contour and dimensioning of the connection points of two complementary semifinished products should therefore be created such that the mechanical integrity of said connection points is always maintained.

As already mentioned a number of times, the electrical conductor is at no point completely sheathed in the region of the connection point. Rather, the connection point has a recess that is continuous in the longitudinal direction of the cable. The shape of this recess corresponds at least largely to the shape of a connection point of a second semifinished product, such that the two connection points, laid on one another, surround the electrical conductor to be contacted (almost entirely) without gaps. The material in the region of the connection point and in the further portions of the cable can be the same, but does not necessarily have to be the same. The same is also true for the material selection of the sheath in the region of the connection point and the further regions of the cable. However, at least the material of the sheath in the region of the connection point and in the other portions of the cable is particularly preferably identical.

The individual cables of the semifinished products therefore have specially formed ends which fit one another in accordance with the key-and-lock principle and, as appropriate, can be laminated on one another by a suitable deformation, such that an electrically faultless and permanent connection is created. The necessary connection of individually produced cables consequently can be established more economically and more reliably.

Cable bundles of individually produced semifinished products can thus be permanently connected for the manufacture of electrodes or catheters by means of an automatable thermal joining process (with application of pressure as appropriate). Here, a plurality of leads electrically insulated from one another can also be reliably contacted within the cable without significantly increasing the electrical resistance. The resultant joint is hermetically sealed and cannot be seen without optical aids.

Catheters and electrodes for medical uses which are produced from flexible printed circuit boards can thus be made longer by means of an interlocking connection. The method according to the present invention also differs from conventional connection methods in that no additional materials (for example, solder material or conductive adhesive) are used. In the method according to the present invention, the electrical contact is established by contact between the metal structures in the region of the connection points. The stability of the electrical connection is provided by the securely surrounding plastics body, which permanently maintains the contact of the metal structures.

Step c) (thermal melting) preferably comprises a heating of the material from a temperature in the range of 80° C. to 450° C. for a period in the range of 1 sec to 30 min. The connection points can also be exposed in step c), or immediately after step c), to a pressure in the range of 1 to 40 bar. Under the specified method conditions, the electrical connection can be established particularly reliably. The thermal melting of the material can be performed or at least assisted in particular by ultrasonic treatment. In accordance with a further preferred variant, the connection between the contact faces of both conductors is supported by an additional ultrasonic treatment before, after, or during the melting.

It is also preferred when the conductor, at least in the region of the contact face of the connection point, consists of a metal layer applied to the sheath. The metal layer can be formed: (i) from at least one noble metal or at least one noble metal alloy, or (ii) from a copper line covered by at least one noble metal or at least one noble metal alloy. In particular, gold, silver, palladium, or alloys thereof are suitable for the aforementioned purposes. The noble metals at the free surface of the conductor prevent the formation of an oxide layer. In particular, the metal layer can have a width ranging from 5 to 100 μm. A thickness of the metal layer lies preferably in the range of from 0.1 to 25 μm. The production of metal layers structured in this way, for example, on a plastics support, is an established technique. In particular, complex conductor structures having a multiplicity of different contact faces and conductors can be produced in this way in highly automated processes.

It is also preferred when the contact face is 1 $\mu m^2$ to 1 $mm^2$ in size.

In accordance with a further embodiment, the metal layer has an elevation, preferably in the region of the contact face. Due to the elevation, for example, in the form of a partially applied particle (or also bond ball) made of a high-grade conductive metal or a metal alloy, in particular, copper, gold, or palladium, the electrical contact can be established particularly reliably and with minimal waste. This particle is deformed during the thermal melting and thus bridges a potential gap between the two conductors to be connected. The contact face can be minimized by the use of the particle.

The thermoplastic material of the sheath is preferably a plastic, in particular, a thermoplastic having a processing temperature of less than 350° C., preferably less than 250° C. The plastic is preferably selected from the group comprising polyethylene (PE), polypropylene (PP), polycarbonate (PC), polyvinyl chloride (PVC), acrylonitrile-butadiene-styrene copolymer (ABS), polyethylene terephthalate (PET), liquid-crystal polymers, polyurethane, polyether ether ketone (PEEK) and copolymers of polyurethane. The plastic is particularly preferably selected from the group comprising liquid-crystal polymers, polyurethane and copolymers of polyurethane. The specified materials are characterized by particularly good processability for the connection method according to the present invention. The connection points of the semifinished products can also be produced particularly easily with use of these materials. By way of example, a metal coating of the specified plastics is readily possible in order to produce the electrical conductors.

As already mentioned, the connection points have to be designed so that their mechanical integrity in the separated semifinished product is ensured and at the same time the connection method according to the present invention is supported. Consequently, the complementary connection points of two semifinished products must be coordinated with one another. This can occur particularly reliably and easily in accordance with a first embodiment, in which the contour of the recess and the sheath in the region of the connection point when combined give a cylinder which surrounds the conductor, and the recess has the shape of a segment of a circle of which the angle subtended by an arc at the center α has a value in the range of from 90° to 270°, in particular 135° to 225°. With segment heights smaller than the radius, the volume of the recess (with the exception of the region of the contact face) can also be limited to the chord of the circle. The segment height of the segment of a circle is then given accordingly.

In a further, preferred embodiment, which can be implemented particularly easily, provision is made so that the contours of the recess and of the sheath in the region of the connection point when combined form a cuboid which surrounds the conductor, and a volume of the recess lies in the range of from 75% to 125% of the volume of the sheath in the region of the connection point. The cuboid of the sheath can, in particular, have a thickness ranging from 10 to 500 μm.

It is also preferred when a contour of the recess is not congruent with a contour of the remaining part of the sheath in the region of the connection point. In accordance with this preferred embodiment, provision is therefore made so that the connection points matching one another of two semifinished products are not completely identical. In this way, semifinished products cannot be connected arbitrarily to one another, and instead only one connection with matching shaping is possible. By way of example, in the case of the above-described cylindrical embodiment of recess and sheath, the angle subtended by an arc at the center in the case of both complementary semifinished products is defined as deviating from 180°. Is also conceivable, in the case of the cuboidal connection point also described above to, define the volume of the recess as unequal to the volume of the sheath in the region of the connection point. Of course, the contour of the recess can be varied arbitrarily in respect of a customization of the connection point.

Further preferred embodiments, features, aspects, objects, advantages, and possible applications of the present invention can be inferred from the dependent claims and the following description in combination with the Figures.

DESCRIPTION OF THE DRAWINGS

The present invention will be explained in greater detail hereinafter on the basis of exemplary embodiments and the associated drawings, in which.

DETAILED DESCRIPTION

Figure 1:
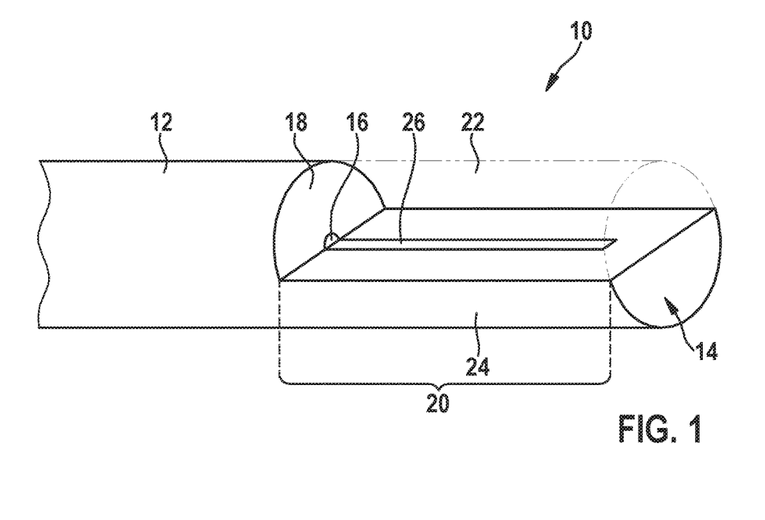
FIG. 1 shows a schematic illustration of part of a semifinished product in the region of the connection point according to the present invention.

FIG. 1 shows, in a heavily schematic way, a region of a semifinished product 10 serving for the production of a flexible electrode or a flexible catheter for medical use. The semifinished product 10 contains, inter alia, a cable 12 having a cable end 14 embodied in a particular way. An electrical conductor 16, which is surrounded by a sheath 18 made of an electrically insulating and thermoplastic material, such as, for example, a liquid-crystal polymer or polyurethane, is disposed in the cable 12. The cable 12 can also have a further sheathing, provided this is advisable for the particular application.

As can be seen, the cable end 14 is part of the cable 12, i.e., the same sheath material is used for the connection point 20 described below in greater detail.

The connection point 20 is characterized in that parts of the sheath 18 have been removed. This therefore results in the recess 22 indicated by the dashed line, and in the embodiment illustrated here the sheath 18 assumes the form of a half-cylinder 24 in the region of the connection point 20. Of course, the angle subtended by an arc at the center α can also be defined as deviating from 180°, such that a contour of the recess 22 and of the sheath 18 in the region of the connection point 20 is no longer identical.

A metal layer 26 is applied to the half-cylinder 24 of the sheath 18 in the region of the connection point 20. By way of example, such a structure can be produced by metal deposition of gold or palladium. It is also conceivable to first apply a copper layer, the surface of which is in turn refined with gold or palladium. The specified materials have a particularly high conductivity.

Figure 2:
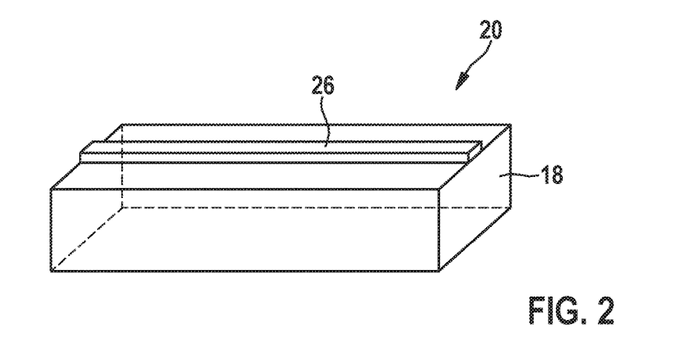
FIG. 2 shows a heavily schematic illustration of a cuboidal connection point in accordance with a further embodiment.

FIG. 2 in a heavily simplified manner shows merely a particular embodiment of the connection point 20 in which the part of the sheath 18 still present assumes the form of a cuboid. A metal layer 26 made of gold is in turn applied to this cuboid. The cuboid can consist of a thermoplastic liquid-crystal polymer.

Figure 3:
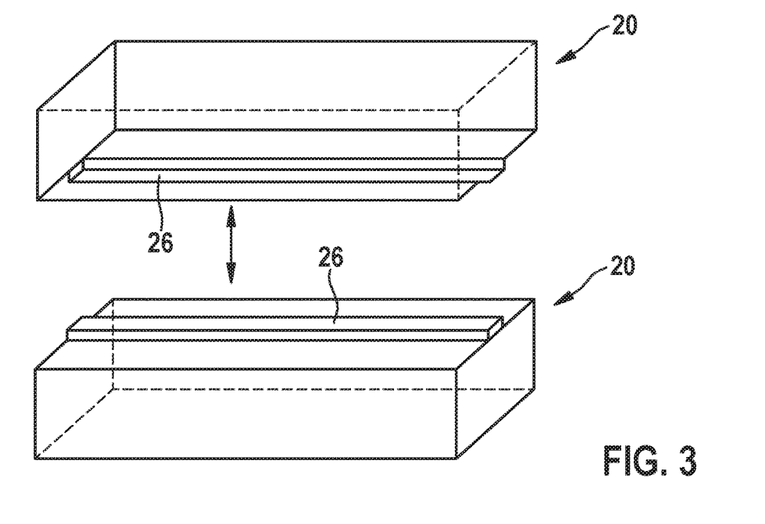
FIG. 3 shows a schematic illustration of two complementary, cuboidal connection points.

FIG. 3 now illustrates how an identically constructed mating piece is oriented and positioned relative to the connection point 20 illustrated in FIG. 2 such that the metal structures come to lie on one another at a point and therefore provide an electrical contact face between the two conductors. Here, connection points 20 each having a conductor 26 running longitudinally are illustrated. However, a plurality of conductors running in parallel or conductors running differently can also be connected to one another. It is also conceivable for the metal structures to contact one another only at individual points when they are laid one on top of the other.

Figure 4:
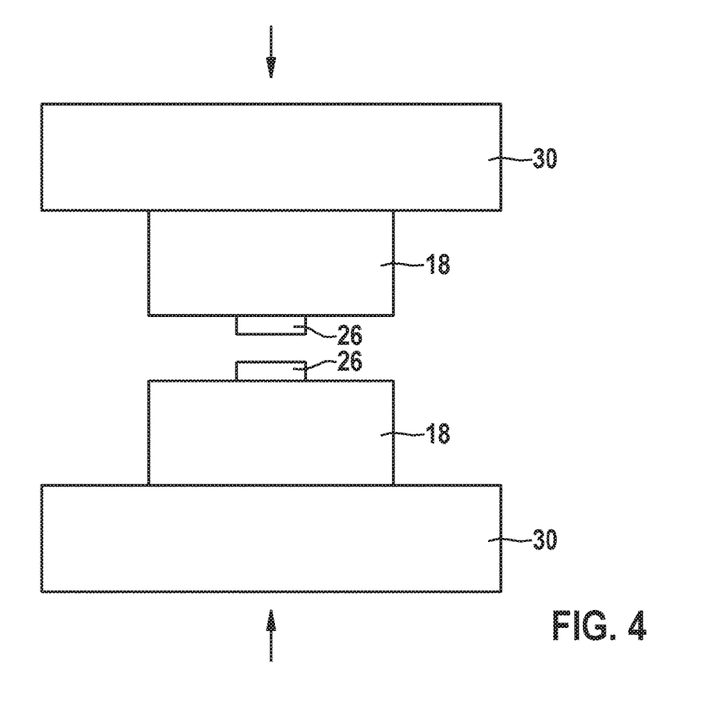
FIG. 4 shows a schematic illustration of the method for producing the electrical connection.
Figure 5:
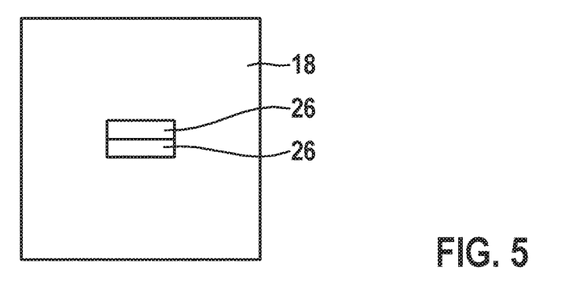
FIG. 5 shows a schematic sectional view through the region of the connection point after completion of the connection method.

By means of a suitable tool 30, for example, a metal die with integrated heater, a pressure of from 1 to 40 bar is applied in order to produce the electrical connection, and the tool 30 is temporarily heated from the ambient temperature to between 80° C. and 450° C. and is cooled again (see FIG. 4). As can be seen, the contact faces of both conductors 26 of the corresponding connection points 20 lie opposite one another. The thermal treatment is maintained for 1 sec to 30 min. After cooling to ambient temperature, the tool 30 is removed again. The tool 30 can have a form which is molded into the plastic material during the heating process. The tool 30 can also be coated with Teflon or a ceramic so as to prevent the thermoplastic from adhering to the tool 30. After the pressing, a homogeneous plastics body is produced, in which the metal layers 26 are embedded in a manner lying against one another (see FIG. 5).

Figure 6:
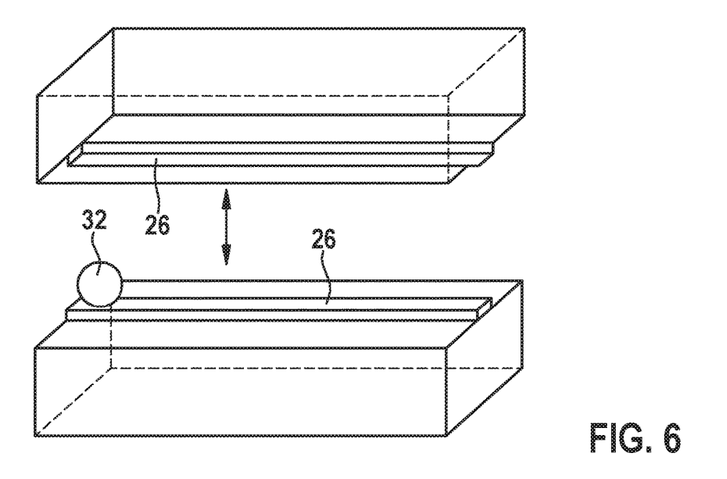
FIG. 6 shows a further alternative embodiment of the connection point.

In order to improve the contact faces between the metal structures and the connection point 20, a gold particle 32 can be added (see FIG. 6). The particle 32 can lie in a small opening in the plastic and is deformed during the pressing.

Figure 7:
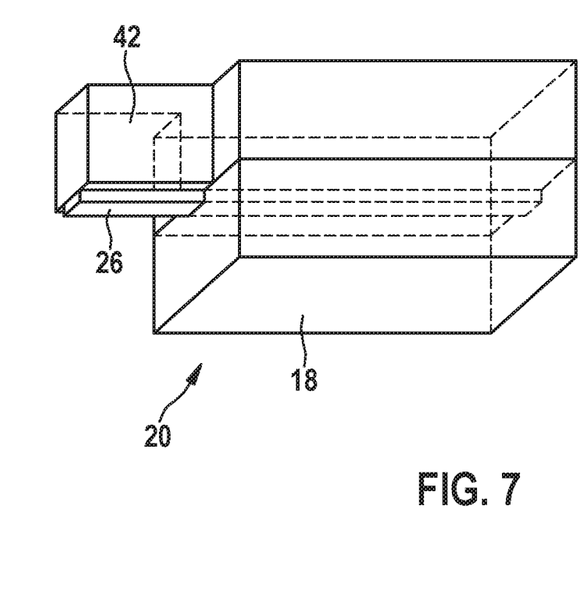
FIG. 7 shows a further schematic illustration of a connection point between two complementary semifinished products in accordance with a further embodiment.

FIG. 7 shows a further embodiment of the connection point 20 of two complementary semifinished products. Here, the two connection points 20 have structures that are coordinated with one another in a matching manner. The connection point 20 illustrated on the left-hand side in FIG. 7 thus forms a niche 40, for which the connection point illustrated on the right-hand side has a corresponding lug 42. In this way, the contact faces of the two conductors 26 can lie on one another in an exact manner. The dimensions, for example, comprise 5 to 100 μm width of the metal structures, 0.1 to 25 μm thickness of the metal structures, and approximately 1 μm$^2$ to 1 mm$^2$ size of the contact face (overlap of opposing metal layers 26).

The metal layers can be applied to the plastic material chemically, electrochemically (galvanically) or by vacuum processes or combinations thereof. It is also conceivable to laminate metal onto the support and to structure this using known methods.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

LIST OF REFERENCE NUMERALS 10 semifinished product
12 cable
14 cable end
16 conductor
18 sheath
20 connection point
22 recess
24 half-cylinder
26 metal layer
30 tool
32 gold particle
40 niche
42 lug

We claim:

1. A semifinished product for producing an electrode lead or a catheter, which semifinished product comprises:
    a cable having at least one electrical conductor, which is embedded in a sheath made of an electrically insulating, thermoplastic material, wherein the cable, at least at one cable end, forms a connection point, via which the conductor can be attached permanently and non-detachably to further components, and wherein:
    part of a surface of the conductor is exposed in a region of the connection point and forms a contact face, and
    the sheath has, in the region of the connection point, a recess that is continuous in a longitudinal direction of the cable,
    wherein contours of the recess and of the sheath in the region of the connection point when combined give a cylinder which surrounds the conductor, and the recess has a shape of a segment of a circle of which an angle subtended by an arc at a center α has a value in a range of from 90° to 270°.

2. The semifinished product according to claim 1, in which the conductor, at least in a region of the contact face of the connection point, consists of a metal layer applied to the sheath.

3. The semifinished product according to claim 2, in which the metal layer is formed: (i) from at least one noble metal or at least one noble metal alloy, or (ii) from a copper line covered by at least one noble metal or at least one noble metal alloy.

4. The semifinished product according to claim 2, in which the metal layer has a width ranging from 5 to 100 μm.

5. The semifinished product according to claim 2, in which the metal layer has a thickness ranging from 0.1 to 25 μm.

6. The semifinished product according to claim 2, in which the metal layer has an elevation in the region of the contact face.

7. The semifinished product according to claim 1, in which the contact face is 1 μm$^2$ to 1 mm$^2$ in size.

8. The semifinished product according to claim 1, in which the thermoplastic material of the sheath is selected from the group comprising polyethylene (PE), poly-propylene (PP), polycarbonate (PC), polyvinyl chloride (PVC), acrylonitrile-butadiene-styrene copolymer (ABS), polyethylene terephthalate (PET), polyether ether ketone (PEEK), liquid-crystal polymers, polyurethane, and copolymers of polyurethane.

9. The semifinished product according to claim 1, in which the arc at the center α has a value in a range of from 135° to 225°.

10. A semifinished product for producing an electrode lead or a catheter, which semifinished product comprises:
    a cable having at least one electrical conductor, which is embedded in a sheath made of an electrically insulating, thermoplastic material, wherein the cable, at least at one cable end, forms a connection point, via which the conductor can be attached permanently and non-detachably to further components, and wherein:
    part of a surface of the conductor is exposed in a region of the connection point and forms a contact face, and
    the sheath has, in the region of the connection point, a recess that is continuous in a longitudinal direction of the cable,
    wherein contours of the recess and of the sheath in the region of the connection point when combined form a cuboid, which surrounds the conductor, and a volume of the recess lies in a range of from 75% to 125% of the volume of the sheath in the region of the connection point, and
    wherein the cuboid of the sheath has a thickness ranging from 10 to 500 μm.

11. A semifinished product for producing an electrode lead or a catheter, which semifinished product comprises:
    a cable having at least one electrical conductor, which is embedded in a sheath made of an electrically insulating, thermoplastic material, wherein the cable, at least at one cable end, forms a connection point, via which the conductor can be attached permanently and non-detachably to further components, and wherein:
    part of a surface of the conductor is exposed in a region of the connection point and forms a contact face, and the sheath has, in the region of the connection point, a recess that is continuous in a longitudinal direction of the cable, wherein a contour of the recess is not congruent with a contour of a remaining part of the sheath in the region of the connection point.

12. The semifinished product according to claim 11, in which the contours of the recess and of the sheath in the region of the connection point when combined form a cuboid, which surrounds the conductor, and a volume of the recess lies in the range of from 75% to 125% of the volume of the sheath in the region of the connection point.

13. A method for producing an electrode line or a catheter, wherein the method comprises the following steps:
   a) providing a first and a second semifinished product, wherein each semifinished product comprises a cable having at least one electrical conductor, which is embedded in a sheath made of an electrically insulating, thermoplastic material, and wherein that the cable, at least at one cable end, forms a connection point via which the conductor can be attached permanently and non-detachably to further components, wherein:
      part of the surface of the conductor is exposed in the region of the connection point and forms a contact face, and
      the sheath has, in the region of the connection point, a recess that is continuous in the longitudinal direction of the cable,
      and wherein a contour of the recesses of the connection point of the first semifinished product corresponds substantially to a contour of the sheath in the region of the connection point of the second semifinished product;
   b) positioning the two semifinished products in a tool in such a way that the connection points rest on one another in a matching manner, such that the contact faces of the two conductors contact one another and the contours of the connection points of the two semifinished products engage with one another; and
   c) thermally melting the thermoplastic material in the region of the connection points.

14. The method according to claim 13, in which step c) (thermal melting) comprises a heating of the material from a temperature in the range of 80° C. to 450° C. for a period in the range of 1 sec to 30 min.

15. The method according to claim 13, in which the connection points in step c) are exposed in step c), or immediately after step c), to a pressure in the range of 1 to 40 bar.

* * * * *